US007736697B2

(12) United States Patent
Thompson et al.

(10) Patent No.: US 7,736,697 B2
(45) Date of Patent: Jun. 15, 2010

(54) ATOMIC LAYER DEPOSITION OF TANTALUM-CONTAINING FILMS USING SURFACE-ACTIVATING AGENTS AND NOVEL TANTALUM COMPLEXES

(75) Inventors: Jeffery Scott Thompson, West Chester, PA (US); Catherine E. Radzewich, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 857 days.

(21) Appl. No.: 11/497,857

(22) Filed: Aug. 1, 2006

(65) Prior Publication Data

US 2007/0036894 A1    Feb. 15, 2007

Related U.S. Application Data

(60) Provisional application No. 60/706,490, filed on Aug. 8, 2005.

(51) Int. Cl.
*C23C 16/00* (2006.01)
*C07F 9/00* (2006.01)

(52) U.S. Cl. .......................... 427/248.1; 556/42; 556/43

(58) Field of Classification Search ........................ None
See application file for complete search history.

(56) References Cited

U.S. PATENT DOCUMENTS

| | | | |
|---|---|---|---|
| 6,511,936 | B1 | 1/2003 | Theopold et al. |
| 6,527,848 | B2 | 3/2003 | Hintermaier et al. |
| 2003/0143839 | A1* | 7/2003 | Raaijmakers et al. ....... 438/633 |
| 2004/0187304 | A1 | 9/2004 | Chen et al. |
| 2004/0219369 | A1* | 11/2004 | Garg et al. .................. 428/446 |
| 2005/0059240 | A1 | 3/2005 | Choi et al. |
| 2007/0003689 | A1 | 1/2007 | Kato et al. |

FOREIGN PATENT DOCUMENTS

WO    WO 03/102265 A1    12/2003

OTHER PUBLICATIONS

M. Ritala et. al., Atomic Layer Deposition in Handbook of Thin Film Materials, 2001, vol. 1, Chapter 2, Academic Press.
Kim et al., "Plasma-enhanced atomic layer deposition of tantalum thin films: the growth and film properties", Preparation and Characterization, Elsevier Netherlands, vol. 441, No. 1-2, 2003, pp. 311-316.
Lemonds, et al., "Surface science investigations of atomic layer deposition half-reactions using TaF5 and Si2H6", Surface Science Elsevier Netherlands, vol. 538, No. 3, 2003, pp. 191-203.
Lehn et al., "A new precursor for the chemical vapor deposition of tantalum nitride films", J. Mater. Chem., Journal of Materials Chemistry, vol. 14, No. 21, 2004, pp. 3239-3245.
Lim et al., "A study on the development of chemical vapor deposition precursors. 4. Syntheses and characterization of new n-alkoxo-[beta]-ketoiminate complexes of niobium and tantalum", Chemistry of Materials, American Chem. Soc., vol. 14, No. 4, 2002, pp. 1548-1554.
Guerin et al., "Conformationally Rigid Diamide Complexes: Synthesis and Structure of Tantalum (III) Alkyne Derivatives", Organometallics, vol. 14, 1995, pp. 3154-3156.
Oshiki et al., "Catalytic performance of tantalum-eta<2>-alkyne complexes [TaCl3 (R<1>C equiv. CR<2>L2] for alkyne cyclotrimerization", Bulletin of the Chemical Society of Japan, vol. 77, No. 5, 2004, pp. 1009-1011.
Franceschini et al., "Volatile Beta-Ketoiminato- and Beta-Diketiminato-Based Zirconium Complexes as Potential MOCVD Precursors" Inorganic Chemistry, Americam Chemical Society, vol. 42, No. 22, 2003, pp. 7273-7282.
PCT International Search Report and Written Opinion for International Application No. PCT/US2006/030711 dated Jan. 3, 2007.

* cited by examiner

*Primary Examiner*—Timothy H Meeks
*Assistant Examiner*—Joseph Miller, Jr.

(57) ABSTRACT

Atomic layer deposition processes for the formation of tantalum-containing films on surfaces are provided. Also provided are novel tantalum complexes that can be used as tantalum precursors in the disclosed deposition processes.

14 Claims, No Drawings

ATOMIC LAYER DEPOSITION OF TANTALUM-CONTAINING FILMS USING SURFACE-ACTIVATING AGENTS AND NOVEL TANTALUM COMPLEXES

FIELD OF THE INVENTION

This invention relates to atomic layer deposition processes for the formation of tantalum-containing films on surfaces in an atomic layer deposition process using surface-activating agents and to novel tantalum complexes useful in the processes.

BACKGROUND

Atomic layer deposition (ALD), also known as atomic layer epitaxy, is a process for depositing highly uniform and conformal thin layers of a metal on a surface. The surface is exposed to vapors of the metal precursor and a reducing agent. Such films have a wide variety of applications in semiconductor microelectronics and optical films. The conventional ALD process, which uses a two-step procedure, is described by M. Ritala and M. Leskela in "Atomic Layer Deposition" in Handbook of Thin Film Materials, H. S. Nalwa, Editor, Academic Press, San Diego, 2001, Volume 1, Chapter 2. Variations of the process have been used to deposit metal-containing layers.

In the typical two-step ALD process, there is a self-limiting adsorption of the metal complex to the surface that is controlled by the interaction of the precursor with the substrate itself in a thermal degradation step. The loss of the ligand is induced thermally, as the metal surface has no functional groups to induce such reactions chemically. It is desired that the metal precursor be stable enough to be transferred into the deposition chamber, but reactive enough to undergo a transformation at the substrate surface.

In a related ALD process the substrate contains functional groups that control the process. These functional groups react chemically with at least one ligand on the metal-containing precursor. For example, the standard process used to prepare conformal $Al_2O_3$ films uses a substrate with hydroxyl groups. The substrate is contacted with $Al(CH_3)_3$, which reacts with the surface hydroxyl groups to form an adsorbed Al—O complex with the liberation of methane. When the surface hydroxyl groups are consumed, the reaction stops. Water is then contacted with the Al—O complex on the surface to generate an aluminum oxide phase and additional hydroxyl groups. The process is then repeated as needed to grow an oxide film of desired thickness. The deposition rate of the $Al(CH_3)_3$ is controlled by the number of surface hydroxyl groups. Once the hydroxyl groups are consumed, no additional $Al(CH_3)_3$ can be adsorbed to the surface.

In the deposition of metal films, there is no reactive group on the substrate surface to initiate the type of self-limiting reaction that occurs in the $Al_2O_3$ case. In these instances, the thermal degradation method is used. For example, in the deposition of a tantalum barrier layer on a tantalum nitride substrate, the self-limiting adsorption is achieved through the thermal decomposition of the tantalum precursor. The tantalum precursor is preferably designed to have the volatility and stability needed for transport to the reaction chamber, but also the reactivity to undergo clean thermal decomposition to allow a metal complex to chemisorb to the substrate surface and to result in tantalum films that are not contaminated with fragments from the tantalum ligands degraded during the thermal deposition.

Tantalum-containing films are useful in integrated circuits and, in particular, tantalum and tantalum nitride films have been used as barrier films.

The processes of the present invention provide a relatively low temperature process for the formation of high quality, uniform tantalum-containing films and provide novel tantalum complexes that that can be used as tantalum precursors in deposition processes.

SUMMARY OF THE INVENTION

One aspect of the present invention is a process for depositing a tantalum-containing film on a surface comprising:

a) exposing the surface of a substrate to a surface-activating agent to form a deposit of a surface-activating complex on the surface;

b) exposing the deposit of the surface-activating complex to a tantalum precursor to form a deposit of tantalum complex on the surface; and c) reacting the deposited tantalum complex with a reagent selected from the group consisting of reducing agents, nitriding agents, and silating agents to form a tantalum-containing film on the surface.

Another aspect of the present invention is a tantalum complex of formula Ta(alkyne)(NRR')$_3$, wherein the alkyne is $R^1CCR^2$, the tantalum is in the +3 oxidation state, and the complex is represented by Structure I

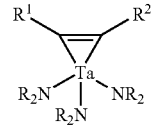

Structure I wherein $R^1$ and $R^2$ are ethyl, and R is independently selected from methyl and ethyl;

$R^1$ is methyl, $R^2$ is phenyl, and R is methyl or ethyl;

$R^1$ and $R^2$ are methyl and R is ethyl;

$R^1$ and $R^2$ are trimethylsilyl and R is ethyl; or $R^1$ is methyl, $R^2$ is trimethylsilyl and R is methyl or ethyl.

A further aspect of the invention is a tantalum complex of formula TaL$_3$, wherein L=β-diketiminate, the tantalum is in the +3 oxidation state, and the neutral form of the β-diketiminate is represented by Structure II

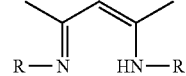

Structure II wherein R is selected from H, —CH$_3$, —CH$_2$CH$_3$, —CH$_2$CH$_2$CH$_3$, and —N(CH$_3$)$_2$.

Another aspect of the present invention is a tantalum complex of formula TaL$_3$, wherein L=N-acetimidoylacetamidine, the tantalum is in the +3 oxidation state, and the neutral form of the N-acetimidoylacetamidine is represented by Structure III.

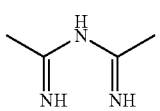

Structure III

Another aspect of the present invention is a tantalum complex having formula $TaL_4$, wherein the tantalum is formally in the +4 oxidation state, and L is selected from the group consisting of N-acetimidoylacetamidine and a β-diketiminate of formula $C_5H_9N_2$. The neutral form of the N-acetimidoylacetamidine is represented by Structure III (as above) and the neutral form of the β-diketiminate is represented by Structure IV.

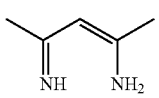

Structure IV

DETAILED DESCRIPTION

One embodiment of the invention is a process comprising the sequential exposure of a surface to a surface-activating agent, a tantalum precursor and a reagent selected from reducing agents, nitriding agents, and silating agents. The first step in the process is exposure of the surface to the surface-activating agent to form a surface-activating complex on the surface. Next, the surface-activating complex reacts with a tantalum precursor to form a non-volatile tantalum complex on the surface in a self-limiting deposition reaction. Finally, the surface-bound complex is reacted with a reagent to generate the desired film. This sequence of reactions can be repeated as many times as necessary to attain the desired film thickness.

In another embodiment the deposited surface-activating complex is exposed to a mixture of the tantalum precursor and the reagent, with the proviso that that there is no gas-phase reaction between the tantalum precursor and the reagent. This process can be repeated as many times as necessary to attain the desired film thickness.

Typically, the processes are conducted in a reaction chamber that can be evacuated, and into which controlled amounts of volatile reagents can be introduced. A means for heating the substrate is also useful.

Suitable substrates include conducting, semi-conducting and insulating substrates, including substrates which are typically used in the electronics industry to manufacture ultra large scale integrated circuits. Suitable substrates typically comprise copper, silicon, silicon dioxide, low k substrates, or low k substrates coated with a barrier layer. Suitable barrier layers include tantalum, tantalum nitride, titanium, titanium nitride, tantalum silicon nitride, titanium silicon nitride, tantalum carbon nitride, tungsten carbonitride, and niobium nitride. "Low k" substrates have a dielectric constant ("k") less than about 4. Suitable low k substrates include doped oxides (e.g., FSG, HSQ, MSQ, HOSP), organics (e.g., SiLK, BCB, FLARE, PAE), highly fluorinated materials (e.g., parylene-F, a-CF, and PTFE), and porous materials (e.g., aerogel and xerogel). Ultra large scale integrated circuits typically contain many millions of gates and hundreds of millions of individual transistors.

In one embodiment, the surface-activating complex is a weak acid (i.e., an acid with a pKa less than 16) that can donate a proton to the tantalum precursor to cause the tantalum complex to lose a ligand and chemisorb to the surface. Alternatively, the surface-activating complex can add to a coordinated ligand, or displace a coordinated ligand from the tantalum coordination sphere to form a new complex. In the absence of the surface-activating agent, there is no adsorption of the tantalum precursor to the surface. The deposition of the surface-activating group can be conducted at temperatures ranging from about room temperature to about 250° C. This is lower than the temperature of a typical thermal degradation process, and thus avoids contamination of the final deposited film by ligands or other decomposition products. Preferably, the surface-activating agent exhibits self-limiting adsorption to the substrate surface and forms a monolayer of the surface-activating complex. Alternatively, the amount of surface-activating agent that is adsorbed can be controlled by limiting the amount of surface-activating agent introduced into the reaction chamber.

The surface-activating agent is chosen to produce a non-volatile complex on the surface. The choice of the surface-activating agent depends on the tantalum precursor, the type of film to be produced and the substrate. The choice of the surface-activating agent also depends on the ligands coordinated to the tantalum ion. The tantalum precursors contain basic ligands, and the surface-activating agent is desirably sufficiently acidic to protonate the coordinated ligand. Imines such as $HN=CR_2$, wherein R is t-butyl, and 1-aminopiperidine and aromatic nitrogen heterocycles such as pyrazole, substituted pyrazoles such as 3,5-dimethylpyrazole, and triazoles such as 1,2,3-triazole, have the desired properties of volatility under use conditions, affinity for metal surfaces and acidity for use as surface-activating agents for the deposition of tantalum-containing films. Desirably, undeposited surface-activating agent is evacuated from the deposition chamber before the tantalum precursor is introduced.

When the deposited surface-activating complex is exposed to a tantalum precursor, a tantalum complex is formed on the surface. The reaction stops when the surface-activating group is consumed. Excess precursor and by-products are removed, e.g., by evacuation or flushing of the chamber.

To be useful in an ALD process, the tantalum precursor is desirably volatile enough to be sublimed without thermal decomposition under the conditions of use. The ligands used in the ALD processes are desirably stable with respect to decomposition and able to desorb from the precursor. Following reduction of or reaction of the tantalum ion, the ligands are liberated and removed from the surface to prevent their incorporation into the tantalum-containing layer being formed.

Tantalum complexes with the tantalum ion in the +3, +4 and +5 oxidation state are especially suitable as tantalum precursors for use in the process.

A group of novel complexes useful as tantalum precursors have the formula $Ta(alkyne)(NRR')_3$, wherein the alkyne is $R^1CCR^2$, and the tantalum is formally in the +3 oxidation state. The neutral form of the tantalum precursor is shown below in Structure I.

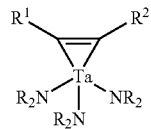

Structure I wherein
$R^1$ and $R^2$ are ethyl, and R is independently selected from methyl and ethyl;
$R^1$ is methyl, $R^2$ is phenyl and R is methyl or ethyl;
$R^1$ and $R^2$ are methyl and R is ethyl;
$R^1$ and $R^2$ are trimethylsilyl and R is ethyl; or
$R^1$ is methyl, $R^2$ is trimethylsilyl and R is methyl or ethyl.

Other novel complexes useful as tantalum precursors include those of formula TaL$_3$, where L=β-diketiminate or N-acetimidoylacetamidine. The tantalum is formally in the +3 oxidation state in these complexes, although the properties of the complex are consistent with a Ta(V) ion and a reduced β-diketiminate or N-acetimidoylacetamidine ligand.

The neutral form of the ligands, L, is shown below in Structures II and III

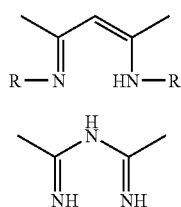

Stucture II

Stucture III wherein R is selected from H, —CH$_3$, —CH$_2$CH$_3$, —CH$_2$CH$_2$CH$_3$, and —N(CH$_3$)$_2$.

The tantalum(III) complexes with ligands of structures II and III can be prepared by the reaction of TaCl$_3$(pyridine)$_3$ with the lithium salt of the ligand in a solvent such as toluene. The Ta(III) starting material is prepared according to the literature procedure (F. A. Cotton, C. A. Murillo, and X. Wang, *Inorganica Chimica Acta*, 245, 115-118 (1996)). In Example 4 below, a preparation of the same compound is described with sodium metal as reducing agent in place of potassium on carbon used in the literature preparation. The lithium salt of the ligand can be prepared by the addition of butyl lithium to the free ligand in a solvent such as toluene. The sodium or potassium salts of the ligand are prepared by reaction of the free ligand with sodium or potassium ethoxide or methoxide in ethanol; the salt is obtained by removal of solvent under vacuum.

Novel complexes with the formula TaL$_4$ are also useful as tantalum precursors, where L=a β-diketiminate of formula C$_5$H$_9$N$_2$ or N-acetimidoylacetamidine (of Structure III, above) and the tantalum is formally in the +4 oxidation state. The neutral form of the β-diketiminate is represented below by Structure IV.

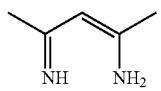

Structure IV

These complexes can be prepared from TaCl$_4$ (described by R. L. Deutscher and D. L. Kepert, Inorganic Chemistry, 9, 2305 (1970)) and the Li$^+$, Na$^+$, or K$^+$ salts of the ligands in solvents such as toluene.

Ta(NEt$_2$)$_2$(NCy$_2$)$_2$ can also be used as a tantalum precursor. This complex has been described by J. M. Lehn et al., Journal of Materials Chemistry 2004, 14, 3239-3245.

A complex with the tantalum formally in the +5 oxidation state that is useful as a tantalum precursor has the formula Ta(NRR')$_5$. R and R' are independently chosen from the group consisting of H, methyl, ethyl, and propyl. These Ta(V) complexes are readily available commercially.

Following the formation of the adsorbed tantalum complex, a reagent selected from the group consisting of reducing agents, nitriding agents, and silating agent is then introduced into the deposition chamber. Typically, the reagent is introduced after any undeposited tantalum precursor and by-products from the reaction of the tantalum precursor with the surface-activating complex have been evacuated from the deposition chamber. Alternatively, the reagent can be introduced along with the tantalum precursor, provided there is no gas phase reaction between the two. In the formation of tantalum metal films, the reagent is usually a reducing reagent such as hydrogen or silane. Reducing agents are preferably volatile and do not decompose on heating. They are also desirably of sufficient reducing power to react rapidly on contact with the tantalum precursor complex adsorbed on the substrate surface. In the formation of a tantalum nitride layer, the reagent is a nitriding agent.

The process can be carried out over a wide range of temperatures, depending on the desired film and application. In one embodiment, the temperature is in the range from about room temperature to about 250° C. In another embodiment, the temperature is in the range from about 60° C. to about 150° C. The process is isothermal; the goal is to have each step in the deposition run in milliseconds and to run at as low a temperature as possible to get a clean film.

The deposition processes of this invention improve upon known processes by allowing the use of lower temperatures and producing higher quality, more uniform films.

EXAMPLES

The present invention is further illustrated by the following Examples. All reagents are available from Sigma-Aldrich Corporation (Milwaukee, Wis.), Acros Organics (Morris Plains, N.J.), or Geleste, Inc. (Morrisville, Pa.). Standard dry box and Schlenk-ware techniques were used in the preparation and handling of the compounds described below. Organic solvents were deaerated with nitrogen and dried over activated 4 Å sieves.

Example 1

This Example demonstrates the preparation of the novel tantalum complex Ta(3-hexyne)(NMe$_2$)$_3$. 18.012 g and 18.057 g of TaCl$_5$ were added to two 250 ml round bottom flasks, respectively. 90 ml of toluene was added to each flask to form an orange/yellow colored solution. 90 ml of ethylene glycol dimethyl ether (DME) was added to each flask while stirring. The solutions turned to an orange/brown color. 4.929 g and 4.941 g of zinc powder was added, respectively, to the two flasks and the solutions were stirred at room temperature for one hour. A yellow precipitate formed in the green solutions as the zinc was consumed. 4.137 g and 4.130 g of 3-hexyne were added, respectively, to the two flasks, and the solutions were heated to reflux in a sand bath for two hr. The solutions turned to a reddish color. The solvent was removed from each flask and the resulting solid material was placed in a thimble and was extracted using a Soxhlet extractor with toluene solvent. The toluene was removed leaving a very tacky orange/brown precipitate. Toluene was added to dissolve the solids; the solution was placed in the freezer overnight. The reaction mixture was filtered through a chilled frit to capture the solid and the solid was dried under vacuum. A total of 14.984 g of the recrystallized solid Ta(EtCCEt)Cl$_3$ (DME) was recovered.

4.500 g Ta(EtCCEt)Cl$_3$(DME) was added to a large round bottom flask with 40 ml of toluene and 40 ml of DME. The solution was a dark brown color. 1.501 g of LiNMe$_2$ was slowly added to the solution with stirring. The solution color turned to a clear reddish color. The reaction mixture was stirred for 1 hour. The solvent was removed under vacuum to yield a brown paste. The material was dissolved in a minimum of hexanes and filtered through Celite® 545 to yield a red solution. The solvent was removed with vacuum, which left a dark brown oily material. The material was purified by sublimation with a dry ice cold finger at 15 mtorr and a temperature range of 60° C. to 100° C. Nuclear magnetic resonance confirmed that the product was Ta(3-hexyne)(NMe$_2$)$_3$.

Example 2

This Example demonstrates the preparation of the novel tantalum complex Ta(MeCCSiMe$_3$)(NEt$_2$)$_3$. 6.001 g of TaCl$_5$ was added to a 250 ml round bottom flask with a stir bar. 50 ml of toluene was added to the flask and the solution turned bright yellow. 50 ml of DME was added slowly with stirring. The solution turned to a light yellow/green color. 1.645 g of zinc powder was added in one portion and the solution color turned to dark green. 1.181 g of 1-(trimethylsilyl)-1-propyne was added and the solution was heated at 55° C. in a sand bath for 3 hr. The solvent was then removed under vacuum, and the material was extracted with toluene and filtered through a sintered-glass frit with Celite® 545. The remaining toluene was removed and hexanes were added. The solids were then captured by filtration and dried. The product yield was 6.520 g. The material was recrystallized from toluene-hexanes at −30° C. The solids were isolated by filtering through a chilled frit and dried. The product yield was 3.610 g. Nuclear magnetic resonance results confirmed that the product was Ta(MeCCSiMe$_3$)Cl$_3$(DME).

2.198 g of Ta(MeCCSiMe$_3$)Cl$_3$(DME) was weighed into a 100 ml round bottom flask with 40 ml of toluene. 1.006 g of LiNEt$_2$ was added slowly to the flask with stirring. The color of the solution changed from dark brown to light brown. The solution was stirred for two hours. The solvent was removed under vacuum. The resulting material was extracted with hexanes and filtered through Celite® 545. Removal of the solvent under vacuum yielded 0.64 g of brown oil. Nuclear magnetic resonance results confirmed that the product was Ta(MeCCSiMe$_3$))(NEt$_2$)$_3$.

Example 3

This Example demonstrates the preparation of the novel tantalum complex Ta(MeCCSiMe$_3$)(NMe$_2$)$_3$. 3.2 g (6.5 mmol) of the Ta(MeCCSiMe$_3$)Cl$_3$(DME) prepared as in Example 2 was dissolved in 40 ml of tetrahydrofuran. 1.0 g (19.6 mmol) of LiNMe$_2$ was added slowly over 10 min. The solution color changed from dark brown to dark red. The reaction mixture was stirred for 1 hr. The solvent was removed under vacuum. The resulting oil was extracted with hexanes; the solution was filtered through Celite® 545. Solvent was removed under vacuum. The product was purified by sublimation and the yield was 1.125 g of dark orange oil. Nuclear magnetic resonance confirmed that the product was Ta(MeCCSiMe$_3$)(NMe$_2$)$_3$.

Example 4

This example demonstrates the preparation of TaCl$_3$(pyridine)$_3$, a starting material for the preparation of Ta(III) complexes. To a 100-mL round-bottom flask were added TaCl$_5$ (2.603 g), 25 mL toluene, and a glass-coated stir bar. Pyridine (10 mL) was added. Sodium powder (0.170 g) was added all at once to the stirred solution. A red color developed immediately. After this solution was stirred at room temperature for several hours, a second portion of Na metal (0.175 g) was added. The reaction mixture was stirred at room temperature overnight to yield a deep blue solution. The reaction mixture was filtered through Celite® 545 to yield a dark blue solution. The Celite® 545 bed was washed with toluene. The resulting solution was concentrated under vacuum to approximately 20 mL. Hexane formed a layer on top of the dark blue solution. The flask was placed in the dry box freezer at −30° C. overnight. A dark blue powder was collected and used in subsequent reactions. This material is stored in the dry box freezer at −30° C.

Example 5

This example demonstrates the preparation of a Ta(III) precursor TaL$_3$ with L=unsymmetrical diketiminate ligand. The ligand (N-isobutyl-N'-methyl-3,5-diketenimine, C$_{10}$H$_{20}$N$_2$) was prepared following the method described by Park and Marshall (*J. Am. Chem. Soc.*, 127, 9330 9331 (2005)). The sodium salt of the diketenimine ligand was prepared by the reaction of sodium ethoxide with the free ligand in toluene, followed by removal of the solvent under vacuum. Sodium hydride (0.051 g) was stirred in 10 mL toluene with a Teflon®-coated stir bar. Ethanol (0.12 mL) was added; vigorous evolution of hydrogen gas was evident. The free ligand was added as an oil. A cloudy solution resulted. Solvents were removed under vacuum. The residue was dissolved in toluene (10 mL). TaCl$_3$(pyridine)$_3$ described in Example 4 above (0.43 g) was added all at once as a solid. The deep blue solution initially formed rapidly turned red. This mixture was stirred for several hours; the solvent was then removed under vacuum to yield a red oil, which was purified by heating in a sublimation apparatus and collecting the oil on a Dry Ice cooled cold finger. This material is very sensitive to the ambient atmosphere.

Example 6

Deposition of Tantalum-Containing Film

Ta(NMe$_2$)$_5$ was used in this example to prepare a tantalum-containing film. The substrate was a gold film (200 A) on silicon prepared by physical vapor deposition. The deposition chamber was a glass tube (one inch in diameter) with connectors to allow introduction of surface-activating agent, precursor, and reducing agent. One end of the tube was fitted with a ground glass joint to allow connection to a glass vacuum line. The other end of the tube was fitted with a tubulator to allow attachment of tubing for introduction of gases. The wafers were placed on the floor of the glass tube. The temperature of the wafer and the precursor were maintained at 80° C. and 70° C., respectively, with heating bands and heating tapes. Pyrazole and dimethylsilane were held at room temperature. Before starting the deposition, the Au wafers were heated at 200° C. under vacuum for 1 hr.

A tantalum-containing film was deposited on the Au wafer in the following manner. Pyrazole was pulsed into the deposition chamber for 10 sec with a helium flow; pressure in the deposition chamber was 150-200 mtorr. The chamber was then purged for 1 min. The Ta(V) precursor was then pulsed into the chamber for 2 min; the pressure in the deposition chamber was 150-200 mtorr. The deposition chamber was then purged for 1 min. Dimethylsilane was pulsed into the deposition chamber by opening the valve of the cylinder containing the reagent and immediately closing it. The deposition chamber was purged for 1 min. This cycle was repeated 100 times to generate a tantalum film.

What is claimed is:

1. An ALD process for depositing a tantalum-containing film on a surface comprising:
   a) exposing the surface of a substrate to a surface-activating agent to form a deposit of a surface-activating complex on the surface, wherein the surface-activating agent is a proton source selected from the group consisting of imines, 1-aminopiperidine and aromatic nitrogen heterocycles;
   b) exposing the deposit of the surface-activating complex to a tantalum precursor to form a deposit of tantalum complex on the surface; and
   c) reacting the deposited tantalum complex with a reagent selected from the group consisting of reducing agents, nitriding agents, and silating agents to form a tantalum-containing film on the surface.

2. The process of claim 1, wherein the tantalum-containing film is tantalum metal and the reagent is a reducing agent.

3. The process of claim 2, wherein the reducing agent is selected from hydrogen and silane.

4. The process of claim 1, wherein the tantalum-containing film is tantalum nitride and the reagent is a nitriding agent.

5. The process of claim 1, wherein the tantalum-containing film is tantalum silicide and the reagent is a silating agent.

6. The process of claim 1 wherein the surface-activating agent is selected from the group consisting of pyrazole, 3,5-dimethylpyrazole, 3,4,5-trimethylpyrazole, 1H-1,2,3-triazole, and 1,2,4-triazole.

7. The process of claim 1, wherein the substrate comprises copper, silicon, silicon dioxide, a low k substrate or a low k substrate coated with a barrier layer.

8. The process of claim 7, wherein the barrier layer is selected from the group consisting of tantalum, tantalum nitride, titanium, titanium nitride, tantalum silicon nitride, titanium silicon nitride, tantalum carbon nitride, tungsten carbonitride, and niobium nitride.

9. The process of claim 1, wherein the tantalum precursor has the formula Ta(alkyne)(NRR')$_3$, wherein the alkyne is R$^1$CCR$^2$, the tantalum is in the +3 oxidation state, and the complex is represented by Structure I

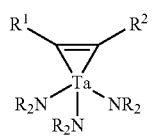

Structure I wherein
   R$^1$ and R$^2$ are ethyl and R is independently selected from methyl and ethyl;
   R$^1$ is methyl, R$^2$ is phenyl and R is methyl or ethyl;
   R$^1$ and R$^2$ are methyl and R is ethyl;
   R$^1$ and R$^2$ are trimethylsilyl and R is ethyl; or
   R$^1$ is methyl, R$^2$ is trimethylsilyl and R is methyl or ethyl.

10. The process of claim 1, wherein the tantalum precursor is a complex having formula TaL$_3$, wherein L=β-diketiminate, the tantalum is in the +3 oxidation state, and the neutral form of the β-diketiminate is represented by Structure II

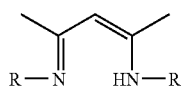

Structure II wherein R is selected from H, —CH$_3$, —CH$_2$CH$_3$, —CH$_2$CH$_2$CH$_3$, and —N(CH$_3$)$_2$.

11. The process of claim 1, wherein the tantalum precursor is a complex having formula TaL$_3$, wherein L=N-acetimidoylacetamidine, the tantalum is in the +3 oxidation state, and the neutral form of N-acetimidoylacetamidine is represented by Structure III

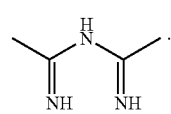

Structure III

12. The process of claim 1, wherein the tantalum precursor is a complex with the formula TaL$_4$, wherein the tantalum is formally in the +4 oxidation state, and L is selected from the group consisting of N-acetimidoylacetamidines and β-diketiminates, wherein the neutral form of the N-acetimidoylacetamidine is represented by Structure III and the neutral form of the β-diketiminate is represented by Structure IV

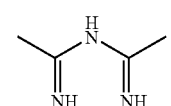

Structure III

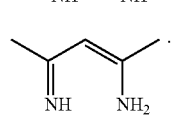

Structure IV

13. The process of claim 1, wherein the tantalum precursor is a complex with the formula Ta(NEt$_2$)$_2$(NCy$_2$)$_2$ and the tantalum is in the +4 oxidation state.

14. The process of claim 1, wherein the tantalum precursor is a complex with the formula the Ta(NRR')$_5$, wherein the tantalum is in the +5 oxidation state, and R and R' are independently selected from the group consisting of H, methyl, ethyl, and propyl.

* * * * *